(12) United States Patent
Ilekti et al.

(10) Patent No.: US 8,802,118 B2
(45) Date of Patent: Aug. 12, 2014

(54) ANHYDROUS FOAM COMPRISING SILICA

(75) Inventors: Philippe Ilekti, Maison-Alfort (FR); Veronique Jacques, l'Hay les Roses (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 13/643,725

(22) PCT Filed: Apr. 29, 2011

(86) PCT No.: PCT/IB2011/051898
§ 371 (c)(1),
(2), (4) Date: Oct. 26, 2012

(87) PCT Pub. No.: WO2011/135543
PCT Pub. Date: Nov. 3, 2011

(65) Prior Publication Data
US 2013/0045261 A1 Feb. 21, 2013

Related U.S. Application Data

(60) Provisional application No. 61/282,988, filed on May 3, 2010.

(30) Foreign Application Priority Data

Apr. 29, 2010 (FR) ..................................... 10 53323

(51) Int. Cl.
*A61K 8/02* (2006.01)
*A61Q 1/04* (2006.01)
*A61Q 19/00* (2006.01)
*A61K 8/92* (2006.01)
*A61K 8/25* (2006.01)

(52) U.S. Cl.
CPC ................ *A61Q 1/04* (2013.01); *A61Q 19/001* (2013.01); *A61K 8/0241* (2013.01); *A61K 8/92* (2013.01); *A61K 8/25* (2013.01); *A61K 2800/60* (2013.01); *A61K 2800/412* (2013.01); *A61K 2201/19* (2013.01)
USPC ....................................................... 424/401

(58) Field of Classification Search
None
See application file for complete search history.

(56) References Cited

U.S. PATENT DOCUMENTS

| 5,266,321 | A | 11/1993 | Shukuzaki et al. |
| 2005/0031655 | A1 | 2/2005 | Karpov |
| 2007/0148114 | A1* | 6/2007 | Jager Lezer et al. ......... 424/70.7 |
| 2008/0070993 | A1* | 3/2008 | Borbely ........................ 514/777 |
| 2008/0233158 | A1* | 9/2008 | Blin et al. ..................... 424/401 |
| 2008/0281008 | A1 | 11/2008 | Styczen et al. |
| 2009/0311348 | A1 | 12/2009 | Einarsson et al. |

FOREIGN PATENT DOCUMENTS

| EP | 0 295 886 A2 | 12/1988 |
| EP | 0 542 669 A1 | 5/1993 |
| EP | 0 787 730 A1 | 8/1997 |
| EP | 0 787 731 A2 | 8/1997 |
| EP | 1 992 324 A1 | 11/2008 |
| EP | 2 127 633 A1 | 12/2009 |
| FR | 2 853 227 A1 | 10/2004 |
| FR | 2 888 476 A1 | 1/2007 |
| FR | 2 931 673 A1 | 12/2009 |
| WO | WO 96/08537 A1 | 3/1996 |
| WO | WO 2008/068323 A1 | 6/2008 |

OTHER PUBLICATIONS

Anonymous, "SUNSIL—Silica Beads for a wide range of make-up applications," http://www.sunjinchem.co.kr/products/SJ_2.1_Silica, pp. 1-25, Sep. 16, 2009.
Hansen, Charles, "The Three Dimensional Solubility Parameter and Solvent Diffusion Coefficient," *J. Paint Technology*, vol. 39, No. 105, 1967.
Written Opinion of the International Searching Authority Issued in Application No. PCT/IB2011/051898; Dated Oct. 11, 2011.
International Search Report issued in Application No. PCT/IB2011/051898; Dated Oct. 11, 2011.

* cited by examiner

*Primary Examiner* — Bethany Barham
(74) *Attorney, Agent, or Firm* — Oliff PLC

(57) ABSTRACT

An anhydrous cosmetic composition in the foam form includes at least one pasty fatty substance in a content of between 10 and 50% by weight, at least one wax in a content of between 4 and 20% by weight, at least one nonvolatile oil in a content of between 40 and 70% by weight and silica in a content of between 3 and 15% by weight, the silica being present in the form of particles exhibiting a mean size of greater than or equal to 0.5 μm and preferably of less than 100 μm.

20 Claims, No Drawings

ANHYDROUS FOAM COMPRISING SILICA

The present invention relates to an anhydrous cosmetic composition in the foam form intended in particular for caring for and/or making up keratinous substances and more particularly the lips, being composed predominantly of fatty substances. The present invention also relates to the associated method for caring for and/or making up keratinous substances. In addition, it relates to a product for making up and/or caring for keratinous substances.

Cosmetic products in the foam form, also known as whipped compositions, exhibit a light and aerated texture. This novel texture renders them particularly pleasant to use, due especially to their particular feel, and is therefore highly appreciated by consumers.

However, such compositions have to be stored at low temperature in a refrigerated environment in order to retain their texture. This is because, above 30° C., whipped compositions become unstable, in other words they lose their texture.

The addition of wax thereto in order to improve the preservation of whipped cosmetic compositions at high temperature is known but such compositions may then be excessively hard and not very pleasant to use.

There thus exists a need for a novel composition exhibiting a satisfactory foam texture which is stable with regard to temperature, in particular for two months at 45° C.

The inventors have thus discovered, surprisingly, that the combination of at least one wax, of a pasty fatty substance and of a nonvolatile oil with silica in given proportions makes it possible to achieve this aim.

Thus it is that the present invention relates, according to one of its aspects, to an anhydrous cosmetic composition in the foam form, comprising, with respect to the total weight of the composition:

(i) at least one pasty fatty substance in a content of between 10 and 50% by weight,
(ii) at least one wax in a content of between 4 and 20% by weight,
(iii) at least one nonvolatile oil in a content of between 40 and 70% by weight, and
(iv) silica in a content of between 3 and 15% by weight, the silica being present in the form of particles exhibiting a mean size of greater than or equal to 0.5 µm and preferably of less than 100 µm, or better still of less than 75 µm, or also of less than 50 µm, and more preferably of less than 25 µm.

Surprisingly, unlike the conventional compositions, the high wax content of which is harmful to the texture of the composition, a composition in the foam form according to the invention exhibits a smooth texture. Such a composition also makes it possible to increase the content of fillers without, however, compromising on glossiness, with respect to the compositions in the form of conventional foams. Such a composition thus makes it possible to provide a glossy deposited layer. This latter property of glossiness is particularly advantageous when the composition is applied to the lips.

A composition according to the invention can thus be intended for caring for and/or making up keratinous substances.

A composition according to the invention can advantageously be a lipstick composition.

A composition according to the invention is anhydrous.

The term "anhydrous composition" is understood to mean in particular that water is not deliberately added to the composition but may be present in the form of traces in the various compounds used in the composition. Thus, preferably, a composition according to the invention comprises less than 3% of water by weight or better still less than 1% of water by weight, with respect to the total weight of the composition.

A composition in accordance with the invention can be coloured or uncoloured.

Another subject-matter of the invention is a method for coating keratinous substances, comprising the application, to the said keratinous substances, of at least one layer of at least one composition in accordance with the invention.

The method for coating keratinous substances according to the invention thus consists in applying, to the said keratinous substances, the composition already in the foam form. In other words, the foam is not created after application of the said composition but is packaged as such. The foam is thus not formed in situ on the keratinous substances. In particular, it is not a delayed-expansion composition, which is a system in which a "volatile" agent is released or formed in the composition after the latter has been applied to the keratinous substances. Specifically, delayed-expansion compositions are created after exposure of a gel to atmospheric pressure and/or to shearing and/or to a temperature greater than ambient temperature.

Finally, a subject-matter of the invention is a product for making up and/or for the nontherapeutic care of keratinous substances comprising:
a composition in the foam form as described above, and
an applicator comprising at least one application component configured in order to apply the said composition to keratinous substances,
a container in which the composition is packaged for storage.

DEFINITIONS

The term "keratinous substances" is understood to mean the skin, the mucous membranes, such as the lips, the nails and the keratinous fibres, such as the eyelashes and the hair. The cosmetic compositions in accordance with the present invention are particularly advantageous for use on the skin and the lips.

The term "lipstick" according to the invention is intended to include a lip balm or a lip gloss or also a lip care product.

The term "composition in the foam form" is understood to mean a composition comprising a gas phase (for example air) in the form of bubbles. Reference is also made to "whipped composition".

The term "whipping agent" is understood to mean a compound capable of conferring, on a composition, the form of a foam with an acceptable degree of whipping.

Throughout the description, including the claims, the expressions "comprising a", "having a" or "exhibiting a" should respectively be understood as being synonymous with "comprising at least one", "having at least one" or "exhibiting at least one", unless the contrary is specified.

Stability

According to the present invention, a composition in the foam form is regarded as stable if the foam "does not collapse" (no subsidence of the composition) and/or if the composition "does not discharge" oil (no phase separation), in particular when the composition remains at 45° C. for two months.

More particularly, the stability (the collapse of the foam and/or the discharge of oil) can be evaluated visually.

Hardness

A composition in the foam form according to the invention can advantageously exhibit a hardness ranging from 40 g to 400 g at 20° C.

Preferably, the composition according to the invention exhibits a hardness ranging from 40 g to 200 g at 20° C.

Preferably, the composition according to the invention exhibits a hardness ranging from 50 g to 150 g at 20° C.

The hardness of a composition according to the invention can be measured using a texture analyser.

This device makes it possible to obtain, for a composition sample, the variation in the resistance to deformation of the composition as a function of the displacement of a rotor into the sample.

The texture analyser measures the strength of resistance to the deformation of the composition as soon as the rotor comes into contact with the sample. After having reached a programmed maximum depth L0 in the sample, the rotor returns to its starting position.

The hardness (expressed in grams or in newtons) is equal to the value for the resistance to the deformation of the composition when the rotor is at the end of the run.

The texture analyser used can in particular be a Stable Micro System TAX-T2i® texture analyser equipped with the Texture Expert Exceed® type operating software and provided with a hemispherical plastic rotor No. 4 with a diameter of 4 mm.

The parameters applied are advantageously as follows:

rate before contact: 2 mm·s$^{-1}$, rate of displacement into the sample: 0.5 mm·s$^{-1}$, maximum depth L0: 2 mm.

The composition samples are prepared in containers with a diameter D>40 mm. The containers are filled with composition in an amount sufficient to eliminate any edge effect. For example, the height for filling with composition in a container is H>25 mm. Two foam containers are thus prepared and then left standing at 20° C. for at least 24 hours before characterization.

At least three measurements are carried out on each sample: one measurement is carried out at the centre of the sample and the other measurements are carried out on points situated equidistantly from the centre and from the edge of the sample.

The hardness is equal to the mean of the measurements carried out (with the minimum number of three).

Compactness

The composition in the foam form according to the invention exhibits in particular a compactness ($c_{foam}$) of less than or equal to 0.9. Preferably, it exhibits a compactness ranging from 0.3 to 0.9, preferably ranging from 0.4 to 0.85 and more preferably ranging from 0.5 to 0.8.

The compactness is measured according to the following protocol: prior to the measurement, the composition in the foam form to be characterized and a container, the volume Vo (in cm$^3$) of which is known with an accuracy of ±0.00005 cm$^3$ (Vo being of the order of 10 cm$^3$), are maintained at a temperature of the order of 20° C. and at atmospheric pressure. The container is weighed by means of a precision balance to ±0.005 g. Its weight is recorded as Wo (in g). This container is carefully filled with the composition in the foam form until the container overflows. The surface of the container is then levelled with a straight blade in order to obtain a perfectly flat foam surface. The weight W (in g) of the container filled with foam is then measured.

The compactness corresponds to the ratio of the density $\rho_v$ of the foam to the density of water (1 g/cm$^3$).

The density of the foam is calculated as follows:

$$\rho_v(g/cm^3) = \frac{W - Wo}{Vo}$$

Degree of Whipping

The degree of whipping corresponds to the amount of gas incorporated in the composition.

The compactness of the composition is measured before and after whipping at 20° C., according to the protocol described above (comment: the compactness of the composition before whipping is measured analogously to the compactness of the whipped composition in the foam form).

The degree of whipping is calculated using the following formula:

Degree of whipping=[(Compactness$_{before\ whipping}$−Compactness$_{foam}$)/Compactness$_{foam}$]×100

The composition according to the invention advantageously exhibits a degree of whipping ranging from 10 to 200%. The degree of whipping can range from 10 to 180%, preferably from 20 to 150% and better still from 25 to 100%, for example ranging from 40 to 100%.

The expression "acceptable degree of whipping" is employed to denote a degree of whipping having a value belonging to the range described above.

Pasty Fatty Substances

Advantageously, the composition of the invention comprises at least one pasty fatty substance.

The term "pasty fatty substance" within the meaning of the present invention is understood to mean a lipophilic fatty compound with a reversible solid/liquid change in state which exhibits, in the solid state, an anisotropic crystalline arrangement and which comprises, at a temperature of 23° C., a liquid fraction and a solid fraction.

In other words, the starting melting point of the pasty fatty substance can be less than 23° C. The liquid fraction of the pasty fatty substance, measured at 23° C., can represent from 9 to 97% by weight of the pasty fatty substance. At 23° C., this liquid fraction preferably represents between 15 and 85% by weight, more preferably between 40 and 85% by weight.

Within the meaning of the invention, the melting point corresponds to the temperature of the most endothermic peak observed by thermal analysis (DSC) as described in Standard ISO 11357-3: 1999. The melting point of a pasty fatty substance can be measured using a differential scanning calorimeter (DSC), for example the calorimeter sold under the name "MDSC 2920" by TA Instruments.

The measurement protocol is as follows:

A 5 mg sample of pasty fatty substance placed in a crucible is subjected to a first rise in temperature ranging from −20° C. to 100° C. at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the enthalpy of fusion consumed at 23° C. to the enthalpy of fusion of the pasty fatty substance.

The enthalpy of fusion of the pasty fatty substance is the enthalpy consumed by the latter to change from the solid state to the liquid state. The pasty fatty substance is "in the solid state" when the whole of its mass is in the solid crystalline form. The pasty fatty substance is "in the liquid state" when the whole of its mass is in the liquid form.

The enthalpy of fusion of the pasty fatty substance is equal to the area under the curve of the thermogram obtained using a differential scanning calorimeter (DSC), such as the calorimeter sold under the name MDSC 2920 by TA Instruments, with a rise in temperature of 5 or 10° C. per minute, according to Standard ISO 11357-3:1999.

The enthalpy of fusion of the pasty fatty substance is the amount of energy necessary to change the pasty fatty substance from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

The liquid fraction of the pasty fatty substance measured at 32° C. preferably represents from 30 to 100% by weight of the pasty fatty substance, preferably from 50 to 100% by weight of the pasty fatty substance, more preferably from 60 to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the enthalpy of fusion consumed at 32° C. to the enthalpy of fusion of the pasty fatty substance. The enthalpy of fusion consumed at 32° C. is calculated in the same way as the enthalpy of fusion consumed at 23° C.

The pasty fatty substance is preferably chosen from synthetic fatty substances and fatty substances of vegetable origin. A pasty fatty substance can be obtained by synthesis from starting compounds of vegetable origin.

The pasty fatty substance is advantageously chosen from:
  lanolin and its derivatives,
  polyol ethers chosen from ethers of pentaerythritol and of polyalkylene glycol, ethers of fatty alcohol and of sugar, and their mixtures. the ether of pentaerythritol and of polyethylene glycol comprising 5 oxyethylene (5 OE) units (CTFA name: PEG-5 Pentaerythrityl Ether), the ether of pentaerythritol and of polypropylene glycol comprising 5 oxypropylene (5 OP) units (CTFA name: PPG-5 Pentaerythrityl Ether), and their mixtures and more particularly the PEG-5 Pentaerythrityl Ether, PPG-5 Pentaerythrityl Ether and soybean oil mixture sold under the name "Lanolide" by Vevy, in which mixture the constituents occur in a ratio by weight of 46/46/8:46% PEG-5 Pentaerythrityl Ether, 46% PPG-5 Pentaerythrityl Ether and 8% soybean oil,
  polymeric or nonpolymeric silicone compounds,
  polymeric or nonpolymeric fluorinated compounds,
  vinyl polymers, in particular:
    olefin homopolymers and copolymers
    hydrogenated diene homopolymers and copolymers,
    linear or branched and homo- or copolymeric oligomers of alkyl(meth)acrylates preferably having a $C_8$-$C_{30}$ alkyl group,
    homo- and copolymeric oligomers of vinyl esters having $C_8$-$C_{30}$ alkyl groups,
    homo- and copolymeric oligomers of vinyl ethers having $C_8$-$C_{30}$ alkyl groups,
  fat-soluble polyethers resulting from polyetherification between one or more $C_2$-$C_{100}$ diols, preferably $C_2$-$C_{50}$ diols,
  esters,
  and/or their mixtures.

The pasty fatty substance is preferably a polymer, in particular a hydrocarbon polymer.

Preference is given, among fat-soluble polyethers, in particular to copolymers of ethylene oxide and/or of propylene oxide with long-chain $C_6$-$C_{30}$ alkylene oxides, more preferably such that the ratio by weight of the ethylene oxide and/or of the propylene oxide to the alkylene oxides in the copolymer is from 5:95 to 70:30. Mention will in particular be made, in this family, of the copolymers such that the long-chain alkylene oxides are positioned in blocks having an average molecular weight of 1000 to 10 000, for example a polyoxyethylene/polydodecyl glycol block copolymer, such as the ethers of dodecanediol (22 mol) and of polyethylene glycol (45 OE) sold under the Elfacos ST9 brand by Akzo Nobel.

Preference is given, among esters, in particular to:
  the esters of an oligomeric glycerol, in particular the esters of diglycerol, especially the condensates of adipic acid and of glycerol, for which a portion of the hydroxyl groups of the glycerols have reacted with a mixture of fatty acids, such as stearic acid, capric acid, isostearic acid and 12-hydroxystearic acid, such as, in particular, those sold under the Softisan 649 brand by Sasol,
  the arachidyl propionate sold under the Waxenol 801 brand by Alzo,
  phytosterol esters,
  triglycerides of fatty acids and their derivatives,
  pentaerythritol esters,
  esters of dimer diol and dimer diacid, if appropriate esterified on their free alcohol or acid functional group(s) by acid or alcohol radicals, in particular dimer dilinoleate esters; such esters can be chosen in particular from esters with the following INCI nomenclature: bis-behenyl/isostearyl/phytosteryl dimer dilinoleyl, dimer dilinoleate (Plandool G), phytosteryl isostearyl dimer dilinoleate (Lusplan PI-DA, or Lusplan PHY/IS-DA), phytosteryl/isostearyl/cetyl/stearyl/behenyl dimer dilinoleate (Plandool H or Plandool S), and their mixtures,
  mango butter, such as that sold under the reference Lipex 203 by AarhusKarlshamn,
  hydrogenated soybean oil, hydrogenated coconut oil, hydrogenated rapeseed oil or mixtures of hydrogenated vegetable oils, such as the soybean, coconut, palm and rapeseed hydrogenated vegetable oil mixture, for example the mixture sold under the reference Akogel® by AarhusKarlshamn (INCI name Hydrogenated Vegetable Oil),
  shea butter, in particular that having the INCI name Butyrospermum Parkii Butter, such as that sold under the reference Sheasoft® by AarhusKarlshamn,
  and their mixtures.

According to a preferred embodiment, the pasty fatty substance is chosen from a mixture of soybean, coconut, palm and rapeseed hydrogenated vegetable oils, shea butter and their mixtures, and more particularly those referenced above.

The pasty fatty substance is present in a composition according to the invention in a content ranging from 10 to 50% by weight, preferably from 10 to 40% by weight, from 15 to 35% by weight, from 20 to 30% by weight, with respect to the total weight of the composition.

Wax

A composition according to the invention comprises at least one wax.

The waxes under consideration in the context of the present invention are generally deformable or nondeformable solid lipophilic compounds at ambient temperature (25° C.) which exhibit a reversible solid/liquid change in state and which have a melting point of greater than or equal to 30° C. which remains at 200° C. and in particular up to 120° C.

On bringing one or more waxes in accordance with the invention to the liquid state (melting), it is possible to render it or them miscible with one or more oils and to form a macroscopically homogeneous mixture of wax(es) and oil(s) but, on bringing the temperature of the said mixture back to ambient temperature, recrystallization of the wax(es) in the oil(s) of the mixture is obtained.

Within the meaning of the invention, the melting point corresponds to the temperature of the most endothermic peak observed by thermal analysis (DSC) as described in Standard ISO 11357-3: 1999. The melting point of the wax can be measured using a differential scanning calorimeter (DSC), for example the calorimeter sold under the name "MDSC 2920" by TA Instruments.

The measurement protocol is as follows:

A 5 mg sample of wax placed in a crucible is subjected to a first rise in temperature ranging from −20° C. to 100° C. at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of wax is measured as a function of the temperature. The melting point of the compound is the value of the temperature corresponding to the tip of the peak of the curve representing the variation in the difference in power absorbed as a function of the temperature.

The waxes capable of being used in a composition according to the invention are chosen from waxes of animal, vegetable, mineral or synthetic origin and their mixtures which are solid at ambient temperature. They can be hydrocarbon, fluorinated and/or silicone waxes.

Preferably, use may in particular be made of hydrocarbon waxes, such as natural beeswax (or bleached beeswax), synthetic beeswax, carnauba wax, rice bran wax, such as that sold under the reference NC 1720 by Cera Rica Noda, candelilla wax, such as that sold under the reference SP 75 G by Strahl & Pitsch, microcrystalline waxes, paraffin waxes and ozokerite, polyethylene waxes or the sunflower seed wax sold by Koster Keunen under the reference sunflower wax.

Mention may also be made of silicone waxes, such as alkyl or alkoxy dimethicones having from 16 to 45 carbon atoms, or fluorinated waxes.

According to a specific embodiment, the wax used in a composition in accordance with the invention exhibits a melting point of greater than 35° C., better still of greater than 40° C., indeed even than 45° C., or also than 55° C.

According to a preferred embodiment, the composition is devoid of silicone wax.

According to a preferred embodiment, the wax is chosen from candelilla wax, rice bran wax, sunflower seed wax and their mixtures, and more particularly those referenced above.

The wax is present in a composition in accordance with the present invention in a content ranging from 4 to 20% by weight, preferably from 5 to 15% by weight, indeed even from 6 to 12% by weight, with respect to the total weight of the composition.

Nonvolatile Oil

A composition according to the invention comprises at least one nonvolatile oil. The term "oil" is understood to mean any fatty substance in the liquid form at ambient temperature (25° C.) and at atmospheric pressure.

The term "nonvolatile oil" is understood to mean any oil having a nonzero vapour pressure at ambient temperature and atmospheric pressure of less than 0.02 mmHg and better still of less than $10^{-3}$ mmHg.

The nonvolatile oil suitable for the preparation of a composition according to the invention may or may not be a hydrocarbon, silicone or fluorinated oil, or a mixture of the latter.

The term "hydrocarbon oil" is understood to mean an oil formed essentially, and even consisting, of carbon and hydrogen atoms, and optionally of oxygen or nitrogen atoms, and not comprising a silicon or fluorine atom. It can comprise alcohol, ester, ether, carboxylic acid, amine and/or amide groups.

The term "silicone oil" is understood to mean an oil comprising at least one silicon atom and in particular comprising Si—O groups.

The term "fluorinated oil" is understood to mean an oil comprising at least one fluorine atom.

The nonvolatile oil can be of animal, vegetable, mineral or synthetic origin.

The nonvolatile oil can be chosen from nonpolar and polar oils and their mixtures.

Nonvolatile Polar Oil

A composition according to the invention can comprise a nonvolatile polar oil.

According to a preferred embodiment, the nonvolatile oil present in the composition according to the invention is a polar oil.

The term "polar oil" is understood to mean, within the meaning of the present invention, an oil having a solubility parameter at 25° C., $\delta_a$, other than 0 $(J/cm^3)^{1/2}$.

The definition and the calculation of the solubility parameter in the Hansen three-dimensional solubility space is described in the paper by C. M. Hansen: "*The Three-Dimensional Solubility Parameters*", J. Paint Technol., 39, 105 (1967).

According to this Hansen space:

$\delta_D$ characterizes the London dispersion forces resulting from the formation of dipoles induced during molecular impacts;

$\delta_p$ characterizes the forces of Debye interactions between permanent dipoles and the forces of Keesom interactions between induced dipoles and permanent dipoles;

$\delta_h$ characterizes the forces of specific interactions (such as hydrogen bonds, acid/base, donor/acceptor, and the like).

$\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

A nonvolatile polar oil used in the invention can be a hydrocarbon, silicone and/or fluorinated oil.

It can be of vegetable, mineral or synthetic origin.

The term "polar hydrocarbon oil" is understood to mean an oil formed essentially, indeed even consisting, of carbon and hydrogen atoms, and of oxygen and/or nitrogen atoms, and not comprising a silicon or fluorine atom. It can comprise alcohol, ester, ether, carboxylic acid, amine and/or amide groups. In particular, a composition according to the invention can comprise a nonvolatile polar oil chosen from the following list of oils, and their mixtures:

vegetable hydrocarbon oils, such as jojoba oil, castor oil, olive oil, sesame oil or liquid triglycerides of fatty acids having from 4 to 10 carbon atoms, such as triglycerides of heptanoic, octanoic or caprylic/capric acids. Mention may in particular be made, as such, of castor oil, such as that sold under the reference Lipovol Co® by Lipo Chemicals, virgin olive oil, such as that sold by AarhusKarlshamn, or triglycerides of caprylic/capric acid, such as those sold under the reference Myritol 318® by Cognis;

hydrocarbon esters of formula RCOOR' in which RCOO represents a carboxylic acid residue comprising from 2 to 30 carbon atoms and R' represents a hydrocarbon chain comprising from 1 to 30 carbon atoms, such as isononyl isononanoate, oleyl erucate or 2-octyldodecyl neopentanoate;

polyesters obtained by condensation of unsaturated fatty acid dimer and/or trimer and of diol, such as those described in Patent Application FR 0 853 634, such as in particular dilinoleic acid and 1,4-butanediol. Mention may in particular be made, as such, of the polymer sold by Biosynthis under the name Viscoplast 14436H (INCI name: dilinoleic acid/butanediol copolymer) or of copolymers of polyols and of dimer diacids, and their esters, such as Hailuscent ISDA sold by Kokyu Alcohol Kogyo, fatty alcohols having from 12 to 26 carbon atoms, such as octyldodecanol, 2-butyloctanol, 2-hexyldecanol, 2-undecylpentadecanol or oleyl alcohol;

fatty acids having from 12 to 26 carbon atoms, such as oleic acid, linoleic acid, linolenic acid and their mixtures;

dialkyl carbonates, it being possible for the 2 alkyl chains to be identical or different, such as dicaprylyl carbonate, sold under the name Cetiol CC® by Cognis; and nonvolatile polar oils of high molecular weight, for example of between 650 and 10 000 g/mol, such as, for example:
vinylpyrrolidone copolymers, such as the vinylpyrrolidone/1-hexadecene copolymer, Antaron V-216, sold or manufactured by ISP (MW=7300 g/mol),
esters, such as:
linear fatty acid esters having a total carbon number ranging from 35 to 70, such as pentaerythrityl tetrapelargonate (MW=697.05 g/mol),
hydroxylated esters, such as polyglycerol-2 triisostearate (MW=965.58 g/mol),
aromatic esters, such as tridecyl trimellitate (MW=757.19 g/mol),
esters of $C_{24}$-$C_{28}$ branched fatty alcohols or fatty acids, such as those described in Application EP-A-0 955 039, in particular triisoarachidyl citrate (MW=1033.76 g/mol), pentaerythrityl tetraisononanoate (MW=697.05 g/mol), glyceryl triisostearate (MW=891.51 g/mol), glyceryl tri(2-decyltetradecanoate) (MW=1143.98 g/mol), pentaerythrityl tetraisostearate (MW=1202.02 g/mol), polyglyceryl-2 tetraisostearate (MW=1232.04 g/mol) or pentaerythrityl tetra(2-decyltetradecanoate) (MW=1538.66 g/mol),
esters and polyesters of dimer diol and of mono- or dicarboxylic acid, such as esters of dimer diol and of fatty acid and esters of dimer diol and of dimer dicarboxylic acid,
sucrose $C_2$-$C_6$ carboxylic acid esters, such as sucrose acetate isobutyrate (SAIB) and more particularly sucrose diacetate hexa(2-methylpropanoate), for example that sold under the name Sustane SAIB Food Grade Kosher by Eastman Chemical,
and their mixtures.

The esters of dimer diol and of monocarboxylic acid can be obtained from monocarboxylic acid comprising from 4 to 34 carbon atoms, in particular from 10 to 32 carbon atoms, which acids are linear or branched and saturated or unsaturated.

Mention may in particular be made, as example of monocarboxylic acid suitable for the invention, of fatty acids.

The esters of dimer diol and of dicarboxylic acid can be obtained from a dimer dicarboxylic acid derived in particular from the dimerization of an unsaturated fatty acid, in particular a $C_8$ to $C_{34}$ unsaturated fatty acid, in particular a $C_{12}$ to $C_{22}$ unsaturated fatty acid, especially a $C_{16}$ to $C_{20}$ unsaturated fatty acid and more particularly a $C_{18}$ unsaturated fatty acid.

According to a specific alternative form, the dimer dicarboxylic acid is more particularly that from which the dimer diol to be esterified also derives.

The esters of dimer diol and of carboxylic acid can be obtained from a dimer diol produced by catalytic hydrogenation of a dimer dicarboxylic acid as described above, for example hydrogenated dilinoleic diacid.

Mention may in particular be made, by way of illustration of dimer diol esters, of the esters of dilinoleic diacids and of dilinoleyl dimer diols sold by Nippon Fine Chemical under the trade names Lusplan DD-DA5® and DD-DA7®.

Preferably, a composition according to the invention comprises a nonvolatile polar oil chosen from triglycerides of fatty acids, vegetable oils, sucrose acetate isobutyrate (SAIB) and their mixtures.

According to a preferred embodiment, a composition according to the invention comprises a nonvolatile polar oil chosen from triglycerides of caprylic/capric acid, castor oil, virgin olive oil, sucrose diacetate hexa(2-methylpropanoate) and their mixtures, in particular those referenced above.

According to a preferred embodiment, the composition comprises at least sucrose acetate isobutyrate (SAIB) and more particularly sucrose diacetate hexa(2-methylpropanoate) as nonvolatile polar oil, for example that sold under the name Sustane SAIB Food Grade Kosher by Eastman Chemical.

Preferably, when a composition according to the invention comprises sucrose acetate isobutyrate, the latter is present in a content of between 0.1 and 15% by weight, preferably between 0.5 and 10% by weight, preferably between 1 and 7% by weight, with respect to the total weight of the composition.

The content of nonvolatile polar oil in the composition according to the invention can vary from 15 to 80% by weight, in particular from 30 to 70% by weight and more particularly from 35 to 70% by weight, with respect to the total weight of the composition.

Preferably, the nonvolatile oil present in a composition according to the invention is a polar oil (or a mixture of polar oils) and is then advantageously present in a content ranging from 40 to 70% by weight, from 45 to 65% by weight, preferably from 50 to 60% by weight, indeed even from 53 to 57% by weight, with respect to the total weight of the composition.

Nonvolatile Nonpolar Oil

A composition according to the invention can comprise a nonvolatile nonpolar oil.

According to one embodiment, the nonvolatile oil present in a composition according to the invention is a nonpolar oil.

The term "nonpolar oil" is understood to mean, within the meaning of the present invention, an oil having a solubility parameter at 25° C., $\delta_a$, equal to 0 $(J/cm^3)^{1/2}$ (the definition and the calculation of the solubility parameters are the same as those given above).

When the nonvolatile oil present in a composition according to the invention is a nonpolar oil, the latter is preferably a hydrocarbon oil.

The term "nonpolar hydrocarbon oil" is understood to mean an oil formed essentially, indeed even consisting, of carbon and hydrogen atoms and devoid of a heteroatom, such as N, O, Si and P.

Mention may be made, as examples of nonvolatile nonpolar hydrocarbon oils suitable for the invention, of hydrocarbon oils, such as squalene, linear or branched hydrocarbons, such as paraffin, petrolatum and naphthalene oils, polybutene, polyisobutene, hydrogenated or partially hydrogenated polyisobutene, isoeicosane, squalane, decene/butene copolymers, polybutene/polyisobutene copolymers, in particular Indopol L-14, polydecenes, such as Puresyn 10, and their mixtures.

Mention may in particular be made of nonvolatile nonpolar hydrocarbon oils of high molecular weight, also known as glossy oils, their molecular weight being, for example, between 650 and 10 000 g/mol, such as, for example:

polybutylenes such as Indopol H-100 (with a molar mass or MW=965 g/mol), Indopol H-300 (MW=1340 g/mol) or Indopol H-1500 (MW=2160 g/mol), sold or manufactured by Amoco, hydrogenated polyisobutylenes, such as Panalane H-300 E, sold or manufactured by Amoco (MW=1340 g/mol), Viseal 20000, sold or manufactured by Synteal (MW=6000 g/mol), or Rewopal PIB 1000, sold or manufactured by Witco (MW=1000 g/mol), polydecenes and hydrogenated polydecenes, such as Puresyn 150 (MW=9200 g/mol), sold by Mobil Chemicals, and their mixtures.

The composition according to the invention can comprise a content of nonvolatile nonpolar oil varying from 15 to 80% by weight, in particular from 30 to 70% by weight and more particularly from 35 to 70% by weight, with respect to the total weight of the composition.

According to a specific embodiment, when the nonvolatile oil present in a composition according to the invention is a nonvolatile nonpolar oil, it is present in a content ranging from 40 to 70% by weight, from 45 to 65% by weight, preferably from 50 to 60% by weight, indeed even from 53 to 57% by weight, with respect to the total weight of the composition.

According to a preferred embodiment, a composition according to the invention comprises at least one nonvolatile (polar or nonpolar) oil of high molecular weight, also known as "glossy oil", the molecular weight of which is, for example, between 650 and 10 000 g/mol, in particular from approximately 750 to approximately 7500 g/mol and more particularly varying from approximately 1000 to approximately 5000 g/mol.

The nonvolatile polar and/or nonpolar oil is present in a composition according to the invention in a content ranging from 40 to 70% by weight, from 45 to 65% by weight, preferably from 50 to 60% by weight, indeed even from 53 to 57% by weight, with respect to the total weight of the composition.

Preferably, the nonvolatile oil is a polar oil advantageously present in a content ranging from 40 to 70% by weight, from 45 to 65% by weight, preferably from 50 to 60% by weight, indeed even from 53 to 57% by weight, with respect to the total weight of the composition.

Volatile Oil

A composition according to the invention can additionally comprise a volatile oil.

The term "volatile oil" is understood to mean an oil (or a nonaqueous medium) capable of evaporating on contact with the skin in less than one hour at ambient temperature and atmospheric pressure. The volatile oil is a volatile cosmetic oil which is liquid at ambient temperature and which has in particular a nonzero vapour pressure at ambient temperature and atmospheric pressure, especially which has a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

A composition according to the invention can comprise a volatile polar or nonpolar oil (the definitions of a polar or nonpolar oil are the same as those given above).

A composition according to the invention can comprise a volatile hydrocarbon, silicone or fluorinated oil.

Mention may be made, as volatile polar hydrocarbon oils which can be used in a composition according to the invention, of ketones which are liquid at ambient temperature, such as methyl ethyl ketone or acetone; short-chain esters, in particular having from 3 to 8 carbon atoms in total, such as ethyl acetate, methyl acetate, propyl acetate or n-butyl acetate, ethers which are liquid at ambient temperature, such as diethyl ether, dimethyl ether or dichlorodiethyl ether; or alcohols, in particular linear or branched lower monoalcohols having from 2 to 5 carbon atoms, such as ethanol, isopropanol or n-propanol.

A volatile polar silicone oil which can be used in the invention can be chosen from silicone oils having a flash point ranging from 40° C. to 102° C., preferably having a flash point of greater than 55° C. and less than or equal to 95° C., and preferentially ranging from 65° C. to 95° C.

Mention may be made, as volatile polar silicone oils which can be used in the invention, of linear or cyclic silicones having a viscosity at ambient temperature of less than 8 centistokes (cSt) ($8\times10^{-6}$ m$^2$/s) and having in particular from 2 to 10 silicon atoms and in particular from 2 to 7 silicon atoms, these silicones optionally comprising alkyl or alkoxy groups having from 1 to 10 carbon atoms. Mention may in particular be made, as volatile silicone oil which can be used in the invention, of dimethicones with a viscosity of 5 and 6 cSt, octamethyl cyclotetrasiloxane, decamethyl cyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Mention may be made, as volatile polar silicone oils which can be used in the invention, of the silicones described in Application FR 0 304 259.

Mention may be made, as volatile polar fluorinated oils which can be used in the invention, of nonafluoromethoxybutane, perfluoromethylcyclopentane and their mixtures.

A volatile nonpolar oil which can be used in the invention can be a volatile nonpolar hydrocarbon oil.

A volatile nonpolar hydrocarbon oil can have a flash point ranging from 40° C. to 102° C., preferably ranging from 40° C. to 55° C. and preferentially ranging from 40° C. to 50° C.

Mention may be made, as volatile nonpolar hydrocarbon oil, of volatile hydrocarbon oils having from 8 to 16 carbon atoms and their mixtures, in particular branched $C_8$-$C_{16}$ alkanes, such as $C_8$-$C_{16}$ isoalkanes (also known as isoparaffins), isododecane, isodecane, isohexadecane and, for example, the oils sold under the Isopar or Permethyl trade names, and their mixtures.

According to one embodiment, a composition according to the invention can comprise a volatile or nonvolatile nonpolar oil chosen from polybutene, polyisobutene, hydrogenated polyisobutene, isododecane, isohexadecane and their mixtures. In a composition according to the invention, the said nonpolar oil can be present in a content varying from 5 to 60% by weight, in particular from 10 to 40% by weight and more particularly from 15 to 35% by weight, with respect to the total weight of the composition.

According to a preferred embodiment, the composition is devoid of volatile oil.

According to a preferred embodiment, the composition according to the invention is devoid of nonpolar oil.

According to a specific embodiment, a composition according to the invention can comprise at least 75% by weight of the combination of the wax, of the nonvolatile oil and of the pasty fatty substance, with respect to the total weight of the composition.

The said combination can be present in a content of greater than or equal to 80% by weight, preferably 85% by weight, indeed even 89% by weight, with respect to the total weight of the composition.

Silica

A composition according to the invention additionally comprises, as inorganic filler, silica in the form of particles exhibiting a mean size of greater than or equal to 0.5 µm. This is because the inventors noticed that the presence of silica particles in a composition according to the invention makes it possible, surprisingly, to stabilize it. Thus, it advantageously retains its foam texture at temperatures which can reach 45° C. and for two months.

Silica "particles" should be understood as meaning, within the meaning of the present invention, colourless or white particles of any shape which are insoluble in the medium of the composition, whatever the temperature at which the composition is manufactured. These particles serve in particular to modify the rheology or the texture of the composition.

The silica particles can exhibit any shape and preferably a spherical or globular shape.

The term "globular" is used to describe a substantially isotropic particle.

Preferably, the mean size of the silica particles in accordance with the invention, or their mean diameter when they are spherical particles, is greater than or equal to 0.6 µm, greater than or equal to 0.8 µm, indeed even greater than or equal to 1.0 µm, greater than or equal to 2 µm, or also greater than or equal to 5 µm. In particular, the mean size of the silica particles in accordance with the present invention can be less than 100 µm, less than 75 µm, less than 50 µm and preferably less than 25 µm.

Characterization of the Size of the Particles

The size of the silica particles can be measured by various techniques. Mention may in particular be made of light scattering techniques (dynamic and static), Coulter counter methods, measurements by rate of sedimentation (related to the size via Stokes' law) and microscopy. These techniques make it possible to measure a particle diameter and, for some of them, a particle size distribution.

Preferably, the sizes and size distributions of the silica particles of the compositions according to the invention are measured by static light scattering using a commercial particle sizer of MasterSizer 2000 type from Malvern. The data are processed on the basis of the Mie scattering theory. This theory, exact for isotropic particles, makes it possible to determine, in the case of nonspherical particles, an "effective" particle diameter. This theory is described in particular in the work by Van de Hulst, H. C., "Light Scattering by Small Particles," Chapters 9 and 10, Wiley, New York, 1957.

The silica particles of a composition according to the invention are characterized by their volume-average "effective" diameter D[4,3], defined in the following way:

$$D[4, 3] = \frac{\sum_i V_i \cdot d_i}{\sum_i V_i}$$

where $V_i$ represents the volume of the particles with an effective diameter $d_i$. This parameter is described in particular in the technical documentation of the particle sizer.

Reference may be made to Standard ISO 13320-1 of September 2000, which describes the measurement of particle sizes.

Mention may in particular be made, as silica particles which can be employed in the present invention, of the thickening precipitated silica sold under the name Sident 22 S® by Evonik Degussa, the hydrated precipitated silica sold under the name Levilite Standard® by CECA, the hydrated silica sold under the name Elfadent SM 514® by Grace Davison, a mixture of silica and polyethylene sold under the name Acematt OK 412® by Evonik Degussa, the hydrated silica sold under the name Tixosil 73® by Rhodia, the hydrated silica sold under the name Zeothix 265® by JM Huber, the hollow silica microspheres sold under the name Silica Beads® by Maprecos, and their mixtures.

Preferably, the silica particles used in the compositions according to the invention are particles of precipitated silicas, without surface treatment.

The silica particles are present in a composition according to the invention in a content ranging from 3 to 15% by weight, preferably from 3 to 10% by weight, from 3 to 8% by weight, from 4 to 7% by weight, indeed even from 4 to 6% by weight, with respect to the total weight of the composition.

According to one embodiment, a composition according to the invention is devoid of elastomer organopolysiloxane.

The term "elastomer" is understood to mean a deformable flexible material having viscoelastic properties and in particular the consistency of a sponge or of a flexible sphere. Its modulus of elasticity is such that this material withstands deformation and has a limited ability to extend and contract. This material is capable of regaining its original shape subsequent to stretching. This elastomer is formed of polymeric chains of high molecular weight, the mobility of which is limited by a uniform network of crosslinking points.

The elastomer organopolysiloxanes preferably excluded from the invention can be solid and partially or completely crosslinked. Included in an oil phase, they are converted, according to the level of oily phase used, from a product with a spongy appearance, when they are used in the presence of low contents of oily phase, to a homogeneous gel in the presence of larger amounts of oily phase. The gelling of the oily phase by these elastomers can be complete or partial.

The elastomeric organopolysiloxanes preferably excluded from the invention are in particular the crosslinked polymers described in Application EP-A-0295886. According to this patent application, they are obtained by an addition and crosslinking reaction, in the presence of a catalyst of the platinum type, of at least:

(a) one organopolysiloxane having at least two lower alkenyl groups per molecule, these alkenyl groups comprising from 2 to 6 carbon atoms; and (b) one organopolysiloxane having at least two hydrogen atoms bonded to a silicon atom per molecule.

The elastomer organopolysiloxanes preferably excluded from the invention are also those described in U.S. Pat. No. 5,266,321. According to this patent, they are in particular:

organopolysiloxanes comprising $R_2SiO$ and $RSiO_{1.5}$ units and optionally $R_3SiO_{0.5}$ and/or $SiO_2$ units, in which the R radicals, independently of one another, represent a hydrogen, an alkyl radical, such as methyl, ethyl or propyl, an aryl radical, such as phenyl or tolyl, or an unsaturated aliphatic group, such as vinyl, the ratio by weight of the $R_2SiO$ units to the $RSiO_{1.5}$ units ranging from 1/1 to 30/1;

organopolysiloxanes which are insoluble and swellable in the silicone oil and which are obtained by addition of an organohydropolysiloxane (1) and of an organopolysiloxane (2) having unsaturated aliphatic groups so that the amount of hydrogen or of unsaturated aliphatic groups in (1) and (2) respectively is between 1 and 20 mol % when the organopolysiloxane is noncyclic and between 1 and 50 mol % when the organopolysiloxane is cyclic.

The elastomer organopolysiloxanes preferably excluded from the invention are, for example, those sold under the names KSG 6 by Shin-Etsu; Trefil E-505C or Trefil E-506C by Dow Corning; Gransil (SR-CYC, SR DMF10, SR-DC556) by Grant Industries, or those sold in the form of preformed gels: KSG 15, KSG 16, KSG 17, KSG 18, KSG 26A, KSG 26B, KSG 41, KSG 42, KSG 43, KSG 44 from Shin-Etsu; Gransil SR 5CYC gel, Gransil SR DMF 10 gel, Gransil SR DC556 gel from Grant Industries; 1229-02-167 and 1229-02-168 from General Electric. Blends of silicone elastomers and in particular the blends of these commercial products are preferably also excluded.

According to a preferred embodiment, a composition according to the invention is such that:
  the pasty fatty substances are preferably chosen from a mixture of soybean, coconut, palm and rapeseed hydrogenated vegetable oils, shea butter and their mixtures, preferably in a content ranging from 20 to 30% by weight, with respect to the total weight of the composition;
  the waxes are preferably chosen from candelilla wax, rice bran wax, sunflower seed wax and their mixtures, preferably in a content ranging from 8 to 12% by weight, with respect to the total weight of the composition;
  the nonvolatile oils are preferably chosen from castor oil, triglycerides of capric/caprylic acid, virgin olive oil, sucrose acetate isobutyrate (SAIB), more particularly sucrose diacetate hexa(2-methylpropanoate), and their mixtures, preferably in a content ranging from 53 to 57% by weight, with respect to the total weight of the composition; and
  the silica particles are preferably present in a content ranging from 4 to 6% by weight, with respect to the total weight of the composition.

Colouring Materials

The composition according to the invention can advantageously comprise a colouring material chosen in particular from dyes (in particular water-soluble or fat-soluble dyes), pigments, pearlescent agents and their mixtures.

The colouring materials can be present in the composition in a content ranging from 0.01 to 15% by weight, with respect to the weight of the composition, preferably from 0.02 to 10% by weight and in particular from 0.05 to 5% by weight, with respect to the total weight of the composition.

The term "pigments" should be understood as meaning white or coloured and inorganic or organic particles of any shape which are insoluble in physiological medium and which are intended to colour the composition.

The pigments can be present in a proportion of 0.01 to 15% by weight, with respect to the weight of the composition, preferably of 0.02 to 10% by weight and in particular of 0.05 to 5% by weight, with respect to the total weight of the composition.

Mention may be made, as inorganic pigments which can be used in the invention, of titanium, zirconium or cerium oxides, and also of zinc, iron or chromium oxides, ferric blue, manganese violet, ultramarine blue and chromium hydrate.

The pigment can also have a structure which can, for example, be of sericite/brown iron oxide/titanium dioxide/silica type. Such a pigment is sold, for example, under the reference Coverleaf NS or JS by Chemicals and Catalysts.

The colouring material can also comprise a pigment having a structure which can, for example, be of the type of silica microspheres comprising iron oxide. An example of a pigment exhibiting this structure is that sold by Miyoshi under the reference PC Ball PC-LL-100 P, this pigment being composed of silica microspheres comprising yellow iron oxide.

Mention may be made, among the organic pigments which can be used in the invention, of carbon black, pigments of D & C type, lakes based on cochineal carmine of barium, strontium, calcium or aluminium, or the diketopyrrolopyrroles (DPPs) described in the documents EP-A-542 669, EP-A-787 730, EP-A-787 731 and WO-A-96/08537.

The term "pearlescent agents" should be understood as meaning coloured particles of any shape, which may or may not be iridescent, produced in particular by certain shellfish in their shells or synthesized, which exhibit a colouring effect by optical interference.

The pearlescent agents can be chosen from pearlescent pigments, such as titanium oxide-coated mica covered with iron oxide, titanium oxide-coated mica covered with bismuth oxychloride, titanium oxide-coated mica covered with chromium oxide or titanium oxide-coated mica covered with an organic dye, and pearlescent pigments based on bismuth oxychloride. They can also be mica particles, at the surface of which at least two successive layers of metal oxides and/or of organic colouring materials are superimposed.

Mention may also be made, as examples of pearlescent agents, of natural mica covered with titanium oxide, with iron oxide, with natural pigment or with bismuth oxychloride.

Mention may be made, among the pearlescent agents available on the market, of the Timica, Flamenco and Duochrome (mica-based) pearlescent agents sold by Engelhard, the Timiron pearlescent agents sold by Merck, the Prestige mica-based pearlescent agents sold by Eckart and the Sunshine synthetic mica-based pearlescent agents sold by Sun Chemical.

The pearlescent agents can more particularly have a yellow, pink, red, bronze, orangey, brown, gold and/or coppery colour or glint.

Mention may in particular be made, by way of illustration of the pearlescent agents which can be employed in the context of the present invention, of pearlescent agents of gold colour sold in particular by Engelhard under the name of Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold in particular by Engelhard under the names Nu Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-coloured pearlescent agents with a gold glint sold in particular by Engelhard under the name Sunstone G012 (Gemtone); pink pearlescent agents sold in particular by Engelhard under the name Tan Opale G005 (Gemtone); black pearlescent agents with a gold glint sold in particular by Engelhard under the name Nu Antique Bronze 240 AB (Timica); blue pearlescent agents sold in particular by Merck under the name Matte Blue (17433) (Microna); white pearlescent agents with a silvery glint sold in particular by Merck under the name Xirona Silver; and golden green pinkish orangey pearlescent agents sold in particular by Merck under the name Indian Summer (Xirona); and their mixtures.

The term "dyes" should be understood as meaning compounds, generally organic compounds, which are soluble in fatty substances, such as oils, or in an aqueous/alcoholic phase.

The fat-soluble dyes can be chosen from Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention can also comprise at least one material with a specific optical effect.

This effect is different from a simple conventional colouring effect, that is to say a unified and stabilized effect such as produced by conventional colouring materials, such as, for example, monochromatic pigments. Within the meaning of the invention, the term "stabilized" means devoid of an effect of variability in the colour with the angle of observation or else in response to a change in temperature.

For example, this material can be chosen from particles with a metallic glint, goniochromatic colouring agents, diffracting pigments, thermochromic agents, optical brighteners and fibres, in particular interference fibres. Of course, these various materials can be combined so as to provide the simultaneous display of two effects.

The particles with a metallic glint which can be used in the invention are chosen in particular from:
  particles of at least one metal and/or of at least one metal derivative,
  particles comprising an organic or inorganic substrate, made of one or more material(s), at least partially covered with at least one layer with a metallic glint comprising at least one metal and/or at least one metal derivative, and
  mixtures of the said particles.

Mention may be made, among the metals which can be present in the said particles, for example, of Ag, Au, Cu, Al, Ni, Sn, Mg, Cr, Mo, Ti, Zr, Pt, Va, Rb, W, Zn, Ge, Te, Se and their mixtures or alloys. Ag, Au, Cu, Al, Zn, Ni, Mo, Cr and their mixtures or alloys (for example, bronzes and brasses) are preferred metals.

The term "metal derivatives" denotes compounds derived from metals, in particular oxides, fluorides, chlorides and sulphides.

Mention may be made, by way of illustration of these particles, of aluminium particles, such as those sold under the names Starbrite 1200 EAC® by Siberline and Metalure® by Eckart.

Mention may also be made of metal powders formed of copper or alloy mixtures, such as the references 2844 sold by Radium Bronze, metal pigments, such as aluminium or bronze, for example those sold under the names Rotosafe 700 from Eckart, silica-coated aluminium particles sold under the name Visionaire Bright Silver from Eckart and particles formed of metal alloy, such as powders formed of bronze (copper and zinc alloy) coated with silica sold under the name Visionaire Bright Natural Gold from Eckart.

The particles can also comprise a glass substrate, such as those sold by Nippon Sheet Glass under the names Microglass Metashine.

The goniochromatic colouring agent can be chosen, for example, from interference multilayer structures and liquid crystal colouring agents.

Examples of symmetrical interference multilayer structures which can be used in compositions produced in accordance with the invention are, for example, the following structures: $Al/SiO_2/Al/SiO_2/Al$, pigments having this structure being sold by DuPont de Nemours; $Cr/MgF_2/Al/MgF_2/Cr$, pigments having this structure being sold under the name Chromaflair by Flex; $MoS_2/SiO_2/Al/SiO_2/MoS_2$; $Fe_2O_3/SiO_2/Al/SiO_2/Fe_2O_3$ and $Fe_2O_3/SiO_2/Fe_2O_3/SiO_2/Fe_2O_3$, pigments having these structures being sold under the name Sicopearl by BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by Merck (Darmstadt). By way of example, these pigments can be pigments with a silica/titanium oxide/tin oxide structure sold under the name Xirona Magic by Merck, pigments with a silica/brown iron oxide structure sold under the name Xirona Indian Summer by Merck and pigments with a silica/titanium oxide/mica/tin oxide structure sold under the name Xirona Caribbean Blue by Merck. Mention may also be made of the Infinite Colours pigments from Shiseido. Different effects are obtained according to the thickness and the nature of the various layers. Thus, with the structure $Fe_2O_3/SiO_2/Al/SiO_2/Fe_2O_3$, the colour changes from green-golden to red-grey for $SiO_2$ layers of 320 to 350 nm; from red to golden for $SiO_2$ layers of 380 to 400 nm; from purple to green for $SiO_2$ layers of 410 to 420 nm; and from copper to red for $SiO_2$ layers of 430 to 440 nm.

Mention may be made, as examples of pigments with a polymeric multilayer structure, of those sold by 3M under the name Color Glitter.

Use may be made, as liquid crystal goniochromatic particles, for example, of those sold by Chemx and of that sold under the name Helicone® HC by Wacker.

Additives

A composition according to the invention can furthermore comprise all the ingredients conventionally used as additives in the cosmetic and dermatological field.

These additives are advantageously chosen from antioxidants, thickeners, sweeteners, basifying or acidifying agents, preservatives and their mixtures.

A composition according to the invention can additionally comprise flavourings and/or fragrances.

Mention may be made, as cosmetic active principles which can be used in the invention, of sunscreens, vitamins A, E, C and B3, provitamins, such as D-panthenol, soothing active principles, such as α-bisabolol, aloe vera, allantoin, plant extracts or essential oils, protecting or restructuring agents, such as ceramides, freshness active principles, such as menthol and its derivatives, emollients (cocoa butter), moisturizing agents (arginine PCA), antiwrinkle active principles, essential fatty acids and their mixtures.

The amounts of these various ingredients are those conventionally used in the fields concerned and vary, for example, from 0.01 to 10% by weight, with respect to the total weight of the composition.

Of course, a person skilled in the art would take care to choose this or these optional additional compounds and/or their amounts so that the advantageous properties of the composition according to the invention are not, or not substantially, detrimentally affected by the addition under consideration.

Preparation Process

A composition employed in the invention can be prepared by a mixing process, followed by the introduction of compressed gas into the said mixture. The gas can be, for example, air, nitrogen-based compounds, carbon dioxide, oxygen or helium.

In particular, the composition is prepared by mixing the ingredients with stirring, generally under hot conditions, and by then whipping under the action of a gas. The gas can be introduced during the stage of cooling the composition or after preparation of the composition, for example using a whipper of Mondomix type, a beater of Kenwood type, a scraped-surface exchanger or a dynamic mixer (of IMT type, for example). The gas is preferably air or nitrogen.

A composition according to the invention can be packaged in a container delimiting at least one compartment which comprises the said composition, the said container being closed by a closure part. The container can be equipped with a means for the dispensing of the said composition. The container can be pot.

The container can be at least partly made of a thermoplastic. Mention may be made, as examples of thermoplastics, of polypropylene or polyethylene. Alternatively, the container is made of nonthermoplastic material, in particular of glass or of metal (or alloy).

The said composition can be applied by finger or using an applicator. The container is preferably used in combination with an applicator comprising at least one application component configured in order to apply the said composition to the lips, such as a brush or a nozzle made of foam.

The examples below are given by way of illustration and without a limiting nature.

EXAMPLES

The compounds used in the examples below are:

| COMPOUND | COMMERCIAL NAME | SUPPLIER |
|---|---|---|
| Castor oil | Lipovol Co | Lipo Chemicals |
| Triglycerides of caprylic/capric acid | Myritol 318 | Cognis |
| Virgin olive oil | Extra Virgin Olive Oil | AarhusKarlshamn |
| Sucrose acetate isobutyrate | Sustane SAIB Food Grade Kosher | Eastman Chemical |
| Mixture of hydrogenated vegetable oils (soybean/coconut/palm/rapeseed) | Akogel | AarhusKarlshamn |
| Shea butter | Lipex Sheasoft | AarhusKarlshamn |
| Candelilla (*euphorbia cerifera*) wax | Candelilla Wax SP 75 G | Strahl & Pitsch |
| Rice bran wax | NC 1720 | Cera Rica Noda |
| Sunflower (*helianthus annuus*) seed wax | Sunflower Wax | Koster Keunen |
| Red 7 | Unipure Red LC 3079 OR | LCW (Sensient) |
| Titanium dioxide | Tipaque PF-671 | Ishihara Sangyo |
| Silica | Sident 22 S | Evonik Degussa |
| Silica dimethyl silylate | Aerosil R 972 | Evonik Degussa |

More particularly, the inorganic fillers mentioned above exhibit the following characteristics:

| Filler | Mean size (µm) |
|---|---|
| Silica | 7 |
| Silica dimethyl silylate | <1 |

Procedure

The make-up compositions illustrated by the examples below are prepared according to the following protocol:

The pigments of the phase C are milled in a portion of the phase A. The remainder of the phase A, the millbase and the waxes of the phase B are added to a jacketed heating vessel. The combined mixture is heated to 100° C. The filler of the phase D (with the exception of Example 1, which does not comprise a filler) is added and the combined mixture is homogenized using a paddle stirrer. The mixture obtained is allowed to cool to 60° C. Air is then incorporated in the mixture using a mechanical whisk while allowing to cool to ambient temperature (25° C.).

The parameters of stability, hardness, compactness and degree of whipping of each composition were measured according to the protocols described above. By contrast, the gloss was evaluated visually.

Examples 1 to 3

Compositions in the Foam Form

Make-up compositions in the foam form were prepared comprising the following ingredients:

| | | Examples (% by weight) | | |
|---|---|---|---|---|
| Phase | Compound | 1 (comparative) | 2 (comparative) | 3 (invention) |
| A | Castor oil | 25.91 | 24.46 | 24.46 |
| | Triglycerides of caprylic/capric acid | 24.94 | 23.55 | 23.55 |
| | Virgin olive oil | 6.78 | 6.40 | 6.40 |
| | Sucrose acetate isobutyrate | 5.38 | 5.08 | 5.08 |
| | Mixture of hydrogenated vegetable oils (soybean/coconut/palm/rapeseed) | 6.48 | 6.12 | 6.12 |
| | Shea butter | 20.22 | 19.09 | 19.09 |
| B | Candelilla (*euphorbia cerifera*) wax | 5.4 | 5.4 | 5.4 |
| | Rice bran wax | 2.47 | 2.47 | 2.47 |
| | Sunflower (*helianthus annuus*) seed wax | 2.34 | 2.34 | 2.34 |
| C | Red 7 | 0.05 | 0.05 | 0.05 |
| | Titanium dioxide | 0.02 | 0.02 | 0.02 |
| D | Silica | | | 5 |
| | Silica dimethyl silylate | | 5 | |
| Total | | 100 | 100 | 100 |

| | Examples | | |
|---|---|---|---|
| Results | 1 (comparative) | 2 (comparative) | 3 (invention) |
| Stability | Phase separation | Release of oil at the surface | stable |

-continued

| Results | Examples | | |
|---|---|---|---|
| | 1 (comparative) | 2 (comparative) | 3 (invention) |
| Hardness (g) | 10 | 100 | 85 |
| Compactness before whipping | 0.94 | 0.94 | 0.96 |
| Compactness after whipping | 0.61 | 0.62 | 0.61 |
| Degree of whipping (%) | 54 | 51.6 | 57.4 |

During application to the lips, the composition of Example 3 is creamy and comfortable for the user.

The stability is subsequently observed after two months at 45° C.

As regards the stability, it is observed:
(i) that the composition of Example 1, devoid of silica, separates into phases and
(ii) that the composition of Example 2, comprising an inorganic filler not in accordance with the present invention, in particular with regard to its size, exhibits release of oil at the surface.
(iii) Conversely, the composition of Example 3 in accordance with the invention exhibits an acceptable stability.

In addition, the composition of Example 3 exhibits a satisfactory hardness.

Finally, it is observed that this composition, deposited on the lips, exhibits a glossy nature.

The invention claimed is:

1. Anhydrous cosmetic composition in the foam form, characterized in that it comprises, with respect to the total weight of the composition:
   (i) at least one pasty fatty substance in a content of between 10 and 50% by weight,
   (ii) at least one wax in a content of between 4 and 20% by weight,
   (iii) at least one nonvolatile oil in a content of between 40 and 70% by weight, and
   (iv) silica in a content of between 3 and 15% by weight, the silica being present in the form of particles exhibiting a mean size of greater than or equal to 0.5 µm.

2. Composition according to claim 1, in which the mean size of the silica particles is greater than or equal to 0.6 µm.

3. Composition according to claim 1, in which the mean size of the silica particles is less than 100 µm.

4. Composition according to claim 1, in which the silica is present in a content ranging from 3 to 10% by weight with respect to the total weight of the said composition.

5. Composition according to claim 1, in which the pasty fatty substance is chosen from a mixture of soybean, coconut, palm and rapeseed hydrogenated vegetable oils, shea butter and their mixtures.

6. Composition according to claim 1, in which the pasty fatty substance is present in a content ranging from 10 to 40% by weight with respect to the total weight of the said composition.

7. Composition according to claim 1, in which the wax is chosen from waxes of animal, vegetable, mineral or synthetic origin and their mixtures which are solid at ambient temperature.

8. Composition according to claim 1, in which the wax is chosen from candelilla wax, rice bran wax, sunflower seed wax and their mixtures.

9. Composition according to claim 1, in which the wax is present in a content ranging from 5 to 15% by weight with respect to the total weight of the composition.

10. Composition according to claim 1, in which the nonvolatile oil is a nonvolatile polar oil.

11. Composition according to claim 10, in which the nonvolatile polar oil is chosen among triglycerides of capric/caprylic acid, castor oil, virgin olive oil, and sucrose diacetate hexa(2-methylpropanoate).

12. Composition according to claim 1, in which the nonvolatile oil is present in a content ranging from 45 to 65% by weight with respect to the total weight of the composition.

13. Composition according to claim 1, exhibiting a degree of whipping ranging from 10 to 200%.

14. Composition according to claim 1, exhibiting a compactness ranging from 0.3 to 0.9.

15. Composition according to claim 1, additionally comprising at least one coloring material.

16. Method for coating keratinous substances, comprising the application, to the said keratinous substances of at least one layer of at least one composition in accordance with claim 1.

17. Composition according to claim 7, in which the wax is chosen among hydrocarbon, fluorinated and/or silicone waxes.

18. Composition according to claim 10, in which the nonvolatile polar oil is chosen among triglycerides of fatty acids, vegetable oils, sucrose acetate isobutyrate and their mixtures.

19. Composition according to claim 15, in which the at least one coloring material is chosen from dyes, pigments, pearlescent agents and their mixtures.

20. Method according to claim 16, in which the keratinous substances are the lips.

* * * * *